United States Patent [19]

Potolsky et al.

[11] Patent Number: 4,619,640
[45] Date of Patent: Oct. 28, 1986

[54] BLOOD TRANSFUSION CONNECTOR ASSEMBLY

[76] Inventors: Abraham I. Potolsky, 1757 Glen Oaks Dr., Montecito, Calif. 93108; Anton J. Blaser, 700 E. Mason St., Santa Barbara, Calif. 93103

[21] Appl. No.: 641,763

[22] Filed: Aug. 17, 1984

[51] Int. Cl.⁴ .............................................. A61M 5/00
[52] U.S. Cl. ......................................... 604/7; 604/48; 604/905; 285/914; 128/912
[58] Field of Search ........................................ 604/4–7, 604/48–53, 93, 175, 905; 285/DIG. 15; 128/912

[56] References Cited

U.S. PATENT DOCUMENTS

| | | | |
|---|---|---|---|
| 2,310,021 | 2/1943 | Heidbrink | 128/204.18 |
| 3,021,840 | 2/1962 | Hallamore et al. | 128/200.21 |
| 3,523,522 | 8/1970 | Whitehead et al. | 128/771 |
| 3,625,212 | 12/1971 | Rosenberg | 604/6 X |
| 3,853,126 | 12/1974 | Schulte | 604/175 X |
| 4,150,673 | 4/1979 | Watt | 604/110 X |
| 4,219,021 | 8/1980 | Fink | 604/248 X |
| 4,280,723 | 7/1981 | Moldestad | 285/DIG. 15 |
| 4,496,349 | 1/1985 | Cosentino | 604/175 |

FOREIGN PATENT DOCUMENTS 670440  9/1963  Canada ...................... 285/DIG. 15

Primary Examiner—Dalton L. Truluck
Attorney, Agent, or Firm—Kelly, Bauersfeld & Lowry

[57] ABSTRACT

A specially designed first adaptor or connector is permanently attached to a blood source secured from a donor and kept at a hospital blood bank. This first connector is color-coded and has the type blood in the source imprinted thereon. Further, it includes a blood carrying projection of given dimensions. A second connector, in turn, is permanently secured to a blood infusion line or tube leading from a potential recipient or patient's vein. This second connector is also color-coded and provided with an imprint of the patient's type blood. Further, the connector includes a blood receiving bore of given dimensions, the color coding, printing of the blood type and the given dimensions for the second connector being determined by the blood type of the patient. When the blood type of the source and the blood type of the patient match, then the first and second connectors are of the same color, have the same blood type printed thereon and the referred to given dimensions of each connector are complementary so that a proper connection can be effected for the transfusion of blood from the source to the patient. If the patient's blood type is different from the source, it is impossible to effect a connection between the first and second connectors so that errors in mismatch are eliminated.

16 Claims, 5 Drawing Figures

BLOOD TRANSFUSION CONNECTOR ASSEMBLY

FIELD OF THE INVENTION

This invention relates generally to medical products and more particularly to a blood transfusion connector assembly for assuring against mismatching of blood transfused into a patient from a source.

BACKGROUND OF THE INVENTION

Blood to be transfused into patients as required in certain medical procedures is normally obtained from a blood bank. This blood bank may be located at the hospital itself. Blood for the blood bank is provided by donors at various blood donation locations. The blood is drawn from the donor at such a location after making a physical check of the donor's health and the stored blood is typed and the specific type imprinted on a plastic container for the blood. It is then transferred to the blood bank.

At the blood bank, a second check of the blood type is normally made to make sure that the bag containing the blood is properly labeled. A specific type of blood is selected from the blood bank to match the patient's blood when a transfusion is to be made. The blood itself is delivered to the patient's room in the hospital and infused by way of a universal connector into a blood infusion tube or line extending to the patient's vein. The patient's blood type is normally checked by the nurse against the type blood in the blood source or bag to make sure that the blood will match.

While every effort is made to check carefully the blood type of the blood source and the blood type of the patient to prevent mismatches, mistakes still occur, usually at the site of the patient. Thus, a selected blood type is delivered to the patient's room but may be transfused into the wrong patient. This mistake more often occurs where there is a ward of several patients. In addition, sometimes a single patient will have multiple blood infusion lines extending to veins at different locations and there is an increased risk of connecting the source blood to an incorrect blood infusion line resulting in a mismatch when several such connecting lines are available.

BRIEF DESCRIPTION OF THE PRESENT INVENTION

With the foregoing in mind, the present invention contemplates a blood transfusion connector assembly which, in effect, avoids any possible mismatch between a source and patient's blood in a transfusion process.

More particularly, in accord with the present invention there is provided a first connector permanently connected to a blood transfusion tube or line extending from a source of blood normally stored at a blood bank. This first connector includes a blood carrying projection of first given dimensions.

A second connector, in turn, is permanently connected to a blood infusion line or tube extending from a patient's vein and includes a blood receiving bore communicating with the blood infusion tube and of second given dimensions.

The second given dimensions are complementary to the first given dimensions of the first connector provided that the blood type of the patient is the same as the blood type of the source so that a connection can only be made by insertion of the projection in the bore if the blood types match.

In addition to making the dimensions of each connector unique to each type of blood, the connectors themselves may be color-coded and have imprinted thereon the blood type involved so that visual inspection will immediately indicate any mismatch between the connector from the blood source and the connector passing to the patient.

Further tactile means may be provided for assuring a nurse or doctor that proper connections are being made.

BRIEF DESCRIPTION OF THE DRAWINGS

A better understanding of this invention will be had by now referring to preferred embodiments thereof as illustrated in the accompanying drawings in which.

DETAILED DESCRIPTION OF THE INVENTION

Figure 1:
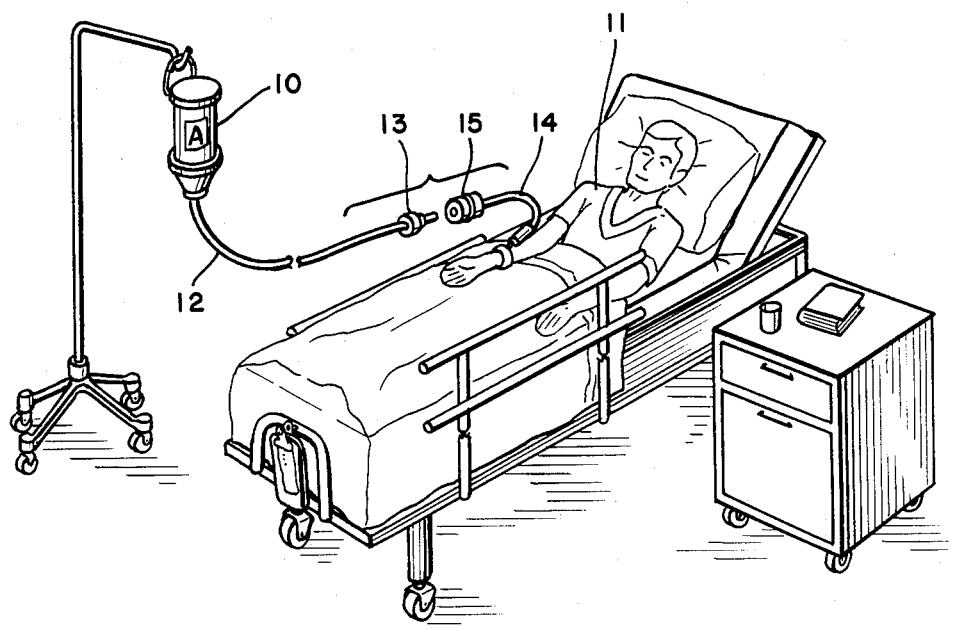
FIG. 1 is a schematic perspective view of a patient in a hospital bed preparatory to receiving a blood transfusion wherein a connector assembly is provided for the blood transfusion components in accord with the present invention.

Referring first to FIG. 1, there is shown a container 10 constituting a source of blood suspended from an I.V. stand for infusion into a patient 11. A blood infusion tube 12 extends from the source 10 and is a permanent attachment to the source. A first connector 13, in turn, is permanently secured to the extending end of the source tube 12.

A second blood infusion line or tube 14 extends from the vein of the patient 11. A second connector 15 is permanently secured to the extending end of the patient tube 14.

The first and second connectors 13 and 15 can only be properly connected together if the blood type of the source blood in the container 10 matches the blood type of the patient 11.

The foregoing is accomplished, briefly, by dimensioning the first connector 13 in a unique manner characteristic of the particular blood type in the container 10. Similarly, the second connector 15 is dimensioned in a unique manner in accord with the blood type of the patient 11. If the blood type of the source 10 and the blood type of the patient 11 match, then the respective dimensioning of the first and second connectors 13 and 14 is the same so that a proper connection can be made. If the blood types do not match, then the dimensions of one of the connectors is different from those of the other and it is not possible to effect a proper connection.

Figure 2:
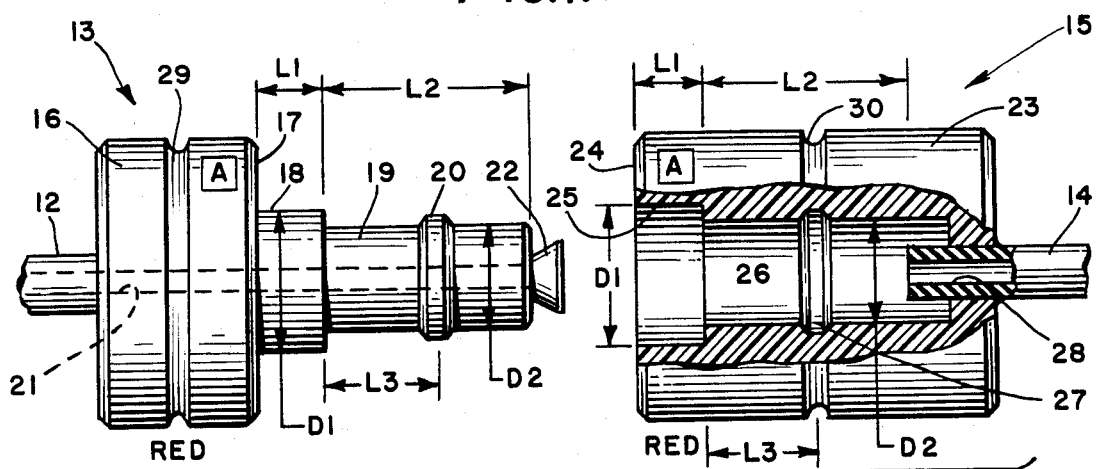
FIG. 2 is a greatly enlarged elevational view partly broken away of the respective first and second connectors making up the blood transfusion connector assembly of this invention.

Referring now to FIG. 2, the first and second connectors 13 and 15 will be described in greater detail.

Referring first to the connector 13, this connector has a first body 16 terminating in a flat face 17. A first cylindrical projection 18 extends a first axial distance L1 from the face 17 and has a first outside diameter D1. A second cylindrical projection 19, in turn, extends a second axial distance L2 from the first cylindrical projection and has a second outside diameter D2 less than the first outside diameter D1. An exterior annular bead 20 circumferentially surrounds the second cylindrical projection 19 at a third axial distance L3 from the first cylindrical projection. The body 16, first cylindrical projection 18, and second cylindrical projection 19 have a continuous axial passageway indicated by the phantom lines at 21 for blood flow through the first connector. The extending end of the second projection 19 preferably terminates in a conically shaped flexible seal 22 the purpose of which will become clearer as the description proceeds.

The first, second and third axial distances L1, L2 and L3 and the first and second diameters D1 and D2 have specific given values in accordance with the blood type in the source container 10 of FIG. 1. In other words, for a different blood type, these dimensions would be different.

Referring now to the second connector 15 connecting to the blood infusion tube or line 14 for the patient 11, this connector includes a second body 23 terminating in a flat face 24 and defining, only in the case of the patient having a blood type the same as the blood type in source 10 of FIG. 1, a first cylindrical bore 25 extending an axial distance equal to the first mentioned axial distance L1 and similarly labeled in FIG. 2 and having an inside diameter equal to the first outside diameter D2 for the first connector and similarly labeled in FIG. 2. The second connector body 23 further defines a second cylindrical bore 26 extending an axial distance equal to the second axial distance L2, this distance being similarly labeled in FIG. 2 for the second connector, and having an inside diameter equal to the second outside diameter D2 for the first connector, also similarly labeled in the second connector of FIG. 2.

Finally, the interior wall of the second cylindrical bore 26 defines an annular groove 27 at an axial distance from the first cylindrical bore equal to the referred to third axial distance L3 for the first connector, this distance also being similarly labeled for the second connector in FIG. 2.

The second cylindrical bore communicates with the patient tube 14 as indicated at the open end 28 of the tube 14 within the second connector body 23.

As mentioned, if the blood types from the source and patient match, then the various dimensions described for the first and second connectors 13 and 15 are compatible. In this event, the first and second cylindrical bores 25 and 26 of the second connector 23 will receive respectively the first and second cylindrical projections 18 and 19 of the first connector 13 and the annular bead 20 will snap into the annular groove 27 when the flat faces 17 and 24 are urged together so that a connection is effected between the blood source and the patient's vein. The connectors themselves are preferably made of plastic and will have a sufficient "give" to permit the snapping action of the bead 20 in the annular groove 27.

In addition to the fact that the dimensions of the first and second connectors are complementary, thus permitting the desired connection to be made and thereby insuring a proper plug match, the colors of the first and second connectors when a proper blood match is made will be the same. In the example of FIG. 2 this color might be red.

Further information in the form of a tactile type coding will also aid in assuring a proper matching. In this respect, the first body 16 for the first connector 13 might be provided with an annular channel such as indicated at 29. The second connector body 23 in turn, would be provided with a similar annular channel 30. If each body contained only one annular channel, then the two connectors would be compatible and would characterize the same blood type. However, if one of the bodies had two annular grooves and the other only one or perhaps three then by "feel" a nurse or doctor could immediately tell that the connectors were mismatched and thus the blood types were mismatched.

It will also be observed from FIG. 2 that the blood type itself may be embossed on each connector. For example, the connector 13 from the blood source is labeled A indicating blood type A. This first connector is permanently attached indicating the blood type in the source at the time a donor gives the blood and is also again checked at the blood bank. In other words, the labeling "A" should match the labeling on the plastic container 10 containing the donor's blood as indicated in FIG. 1.

Similar embossing of the blood type characteristic of the patient would be provided on the patient connector body 23 as shown in FIG. 2.

When the first connector 13 is connected to the second connector 23 as described with respect to FIG. 2, it will be appreciated that the conical flexible seal 22 on the end of the second projection 19 in the connector 16 will engage about the periphery of the end opening portion 28 of the patient infusion tube 14 within the second cylindrical bore 26. When the bead 20 snaps into the groove 27, the flexible seal 22 will be held in tight engagement so that proper passage of blood through the passageway 21 of the connector and into the patient infusion tube 14 will be carried out.

It can be appreciated from the foregoing that should any of the dimensions L1, L2 and L3 or D1 and D2 differ between the first and second connectors, a proper connection could not be effected.

Figure 3:
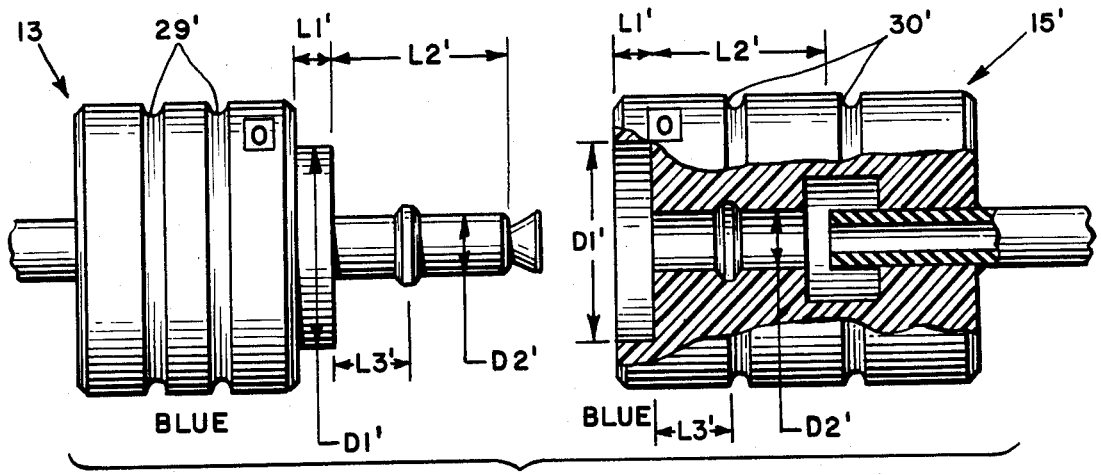
FIG. 3 is a view similar to FIG. 2 illustrating connectors having different dimensional characteristics for indicating a different blood type.

Referring now to FIG. 3, there are shown further first and second connectors indicated generally by the numerals 13' and 15' having dimensions, color coding and embossing printing characteristic of blood types different from those for the connectors described in FIG. 2. In the example of FIG. 3, the connectors are characteristic of the blood type O and this letter accordingly is embossed on the connectors. In addition, there are shown two exterior annular channels at 29' for the first connector 13' and at 30' for the second connector 15' thereby indicating that these connectors are associated with a different blood type from the connectors of FIG. 2. Also, variations in the dimensions L1, L2 and L3 and in the dimensions D1 and D2 from those of FIG. 2 for the two connectors are indicated in FIG. 3 at L1', L2' and L3' and D1' and D2'.

While the connectors 13' and 15' in FIG. 3 have complementary dimensions so that they can be properly coupled together, it will be immediately evident that the first connector 13' of FIG. 3 could not be properly connected to the second connector 15 of FIG. 2. Similarly the first connector 13 of FIG. 2 could not be received in the second connector 15' of FIG. 3. Thus, mismatching of a Type A blood with Type O blood is impossible, in that the first and second connectors could not be connected together if such a mismatch occurred.

Figure 4:
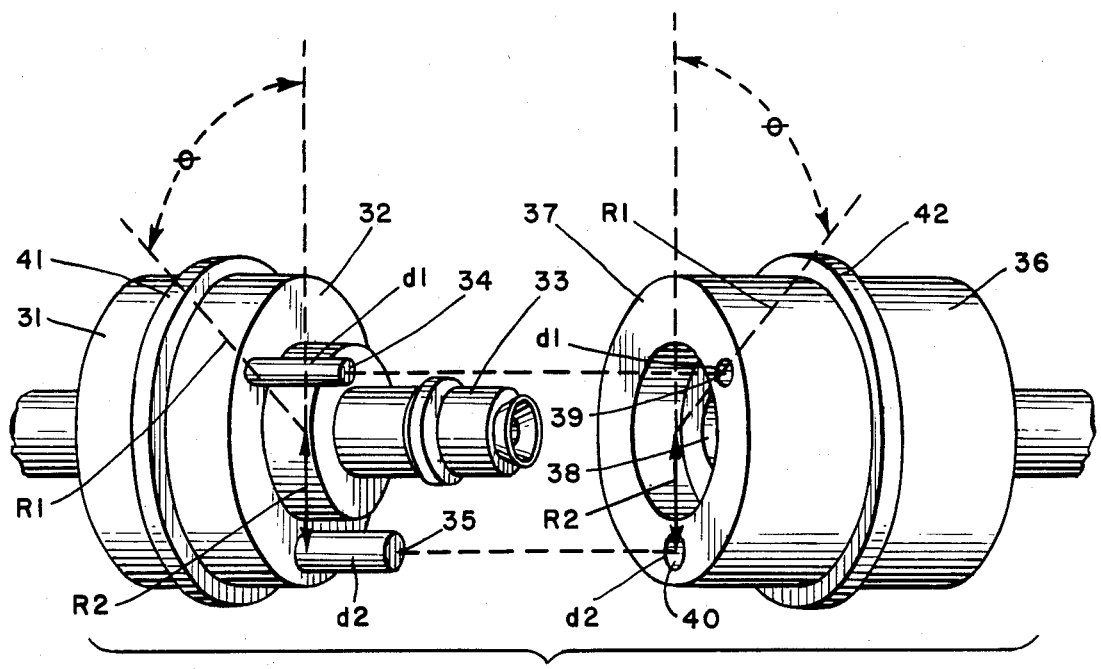
FIG. 4 is a perspective view of connectors preparatory to being connected together wherein the same are characterized by additional means for assuring a proper matching; and, FIG. 5 is another perspective view similar to FIG. 4 showing yet a further embodiment of the connectors.

Referring now to FIG. 4 there is shown another embodiment of the invention wherein again there is provided a first connector having a first body 31 terminating in a flat face 32. A projection 33 extends from the face and in addition, there are provided radially spaced thin cylindrical projections 34 and 35 extending from the flat face 32. If one of these projections such as projection 35 lies on the vertical, the other is circumferentially displaced by the angle $\theta$. Further, the projections 34 and 35 have different outside diameters indicated at d1 and d2. Also, the radial distances R1 and R2 that the projections 34 and 35 are spaced from the axis of the connector may vary.

Referring now to the second connector shown in FIG. 4, this connector includes a body 36 having a flat face 37 defining an inner bore 38 for receiving the second projection 33 of the connector body 31. Also, the flat face 37 includes smaller diameter radially displaced bores 39 and 40 having inside diameters d1 and d2 dimensioned to receive the projections 34 and 35 for the first connector body 31. In this respect, the cylindrical bore 39 is circumferentially displaced from the vertical by the same angle $\theta$. Finally, the inside diameters correspond to the outside diameters of the projections 34 and 35 so that mating is positive. It will be understood that the parameters R1 and R2 designating the radial distances of the projections, and the diameters d1 and d2 will correspond to the cylindrical bores in the second connector body 36 when a proper blood match is realized.

FIG. 4 illustrates a further tactile means for assuring that the connectors are compatible together, this tactile means taking the form of an annular rib 41 on the first connector body 31 and an annular rib 42 on the second connector body 36. If there is only one such rib on each connector, then by "feel" a doctor or nurse will know that the two connectors are compatible and each represent the same blood type.

Figure 5:
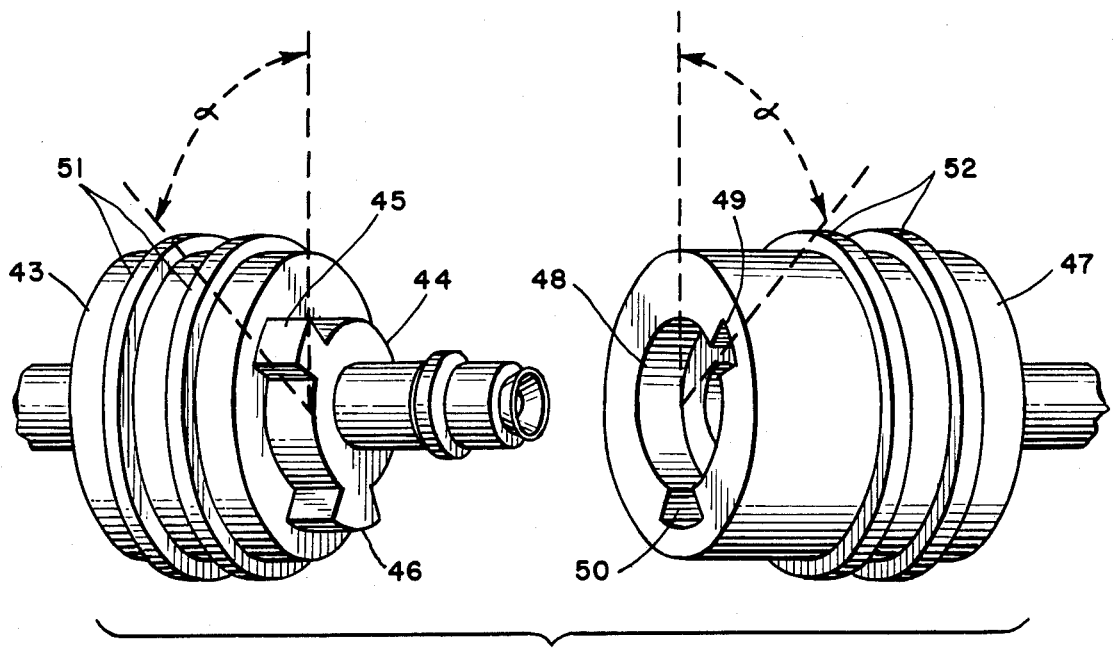

FIG. 5 illustrates yet another embodiment of the invention wherein there is provided a first connector body 43 having a first projection 44 with radially extending ears 45 and 46. The second connector body 47, in turn, has a cylindrical bore 48 with radially extending notches 49 and 50 dimensioned to receive the ears 45 and 46 provided that the blood types represented by the connectors are the same. In this respect, the circumferential offset from the vertical of the ear 45 and the corresponding notch 49 is the same and is represented by the angle.

Provided that the connectors represent the same blood type, then the ears can be received in the notches and a proper connection effected. If the blood types differ, then the offset angles and/or other dimensions will differ and a proper connection cannot be made.

In FIG. 5, the blood type represented by the connectors is different from that of FIG. 4. Accordingly, there might, by way of example, be provided two annular ribs indicated at 51 for the first connector body 43 and at 52 for the second connector body 47. These pair of ribs on each body will indicate to a nurse or doctor tactilely that the connectors are properly matched.

The provision of the additional projections 34 and 35 described in FIG. 4 and/or radial ears such as at 45 and 46 described in FIG. 5 permit many more combinations of dimensions for the connectors to be realized.

As mentioned heretofore, the first connector having dimensions, color coding and an embossed imprinting of the blood type is matched with the blood source of a donor at the time the donor contributes the blood and also a second check is made at the blood bank to make sure that the blood type designated by the connector corresponds to the blood source with which the connector communicates. In permanently securing the second connector to the blood infusion line or tube extending to the patient, after the patient's blood has been typed, a nurse will order the second connector for the patient from the pharmacist who will double check the blood type so that there are two independent persons in the form of the nurse and pharmacist double-checking that the proper patient connector designates a blood type corresponding to that of the patient.

It should also be understood that the patient connector or second connector for the patient is disposable and is dedicated to only a single patient. In other words, it is never used with another patient, even though the other patient may have the same blood type. This disposability avoids possible contamination should a patient be afflicted with a disease such as AIDS or the like.

From all of the foregoing it will now be evident that the present invention has provided a unique blood transfusion connector assembly which will assure against certain types of mistakes being made in the transfusion of blood from a source to a patient.

We claim:

1. A connector assembly for use in assuring a proper blood type match when transfusing blood from a source to a patient, including:
    (a) a plurality of first connectors each adapted to communicate with said source of different blood type and including a blood carrying projection of first given dimensions differing from said first given dimensions of the remaining ones of said first connectors;
    (b) a plurality of second connectors each adapted to communicate with a vein in said patient and defining a blood receiving bore for communication with the patient's blood of different blood type and of second given dimensions differing from said second given dimensions of the remaining ones of said second connectors, said second given dimensions being complementary to said first given dimensions so that said first connectors are matably connectable each with only a respective one of said second connectors and only if the source and patient blood types associated with the first and second connectors match, any difference in said first and second dimensions preventing a proper connection from being carried out so that is is not possible to transfuse blood of one type into a patient having blood of another type; and
    additional means on each of said first connectors and each of said second connectors for indicating a match between the source and the patient blood type and thereby further indicating that a proper connection can be made between said first and second connectors.

2. An assembly according to claim 1, in which said first given dimensions for each of said first connectors includes the length and outside diameter of said projection and said second given dimensions for each of said second connectors includes the length and inside diameter of said bore.

3. An assembly according to claim 1, in which each of said first projections includes an annular bead at a given axial distance therealong, said axial distance constituting one of said first dimensions, said bore for each of said second connectors having an internal annular groove at a given axial distance therealong constituting one of said second dimensions such that when the axial distance of the bead corresponds to the axial distance of the groove, the bead can snap into the groove and effect a proper connection between the first and second connectors.

4. A connector assembly for use in assuring a proper blood type match when transfusing blood from a source to a patient including, in combination:
  (a) a source tube extending from said source;
  (b) a first connector permanently secured to the extending end of said source tube, said first connector having:
    (1) a first body terminating in a flat face;
    (2) a first cylindrical projection extending a first axial distance from said face and having a first outside diameter;
    (3) a second cylindrical projection extending a second axial distance from said first cylindrical projection and having a second outside diameter less than said first outside diameter; and
    (4) an external annular bead circumferentially surrounding said second cylindrical projection at a third axial distance from said first cylindrical projection, said body, first cylindrical projection and second cylindrical projection having a continuous axial passageway for blood flow through said first connector, the first, second and third axial distances on the first and second outside diameters having specific given values in accordance with the blood type in said source;
  (c) a patient tube adapted to extend from said patient's vein;
  (d) a second connector permanently secured to the extending end of said patient tube, said second connector having:
    (1) a second body terminating in a flat face and defining, only in the case of a patient having a blood type the same as said source;
    (2) a first cylindrical bore extending an axial distance equal to said first axial distance and having an inside diameter equal to said first outside diameter, said body further defining:
    (3) a second cylindrical bore extending an axial distance equal to said second axial distance and having an inside diameter equal to said second outside diameter, the interior wall of said second cylindrical bore defining an annular groove at an axial distance from said first cylindrical bore equal to said third axial distance, said second cylindrical bore communicating with said patient tube, said first and second cylindrical bores receiving said first and second cylindrical projections and said annular bead snapping into said annular groove when the flat faces of said first and second bodies are urged together so that a connection is effected between said blood source and the patient's vein, it being assured that whenever the connectors can be connected as described, there is a proper match of source and patient blood type; and
  additional means on said first and second connectors for indicating a match between the source and the patient blood type and thereby further indicating that a proper connection can be made between said first and second connectors.

5. An assembly according to claim 4, in which said additional means includes at least one annular exterior channel on said first body and at least one annular exterior channel on said second body, the number of channels on said first body and the number of channels on said second body being equal only when the source and patient blood type match.

6. An assembly according to claim 4, in which said additional means includes at least one annular rib on said first body and at least one annular rib on said second body, the number of annular ribs on said first body and the number of annular ribs on said second body being equal only if the source and patient blood type match.

7. An assembly according to claim 4, in which said additional means comprises nomenclature on said first body indicating the blood type of the source and nomenclature on said second body indicating the blood type of the patient.

8. An assembly according to claim 4, in which said additional means comprises an exterior color on said first body characteristic of the blood type of the source and an exterior color on said second body characteristic of the blood type of the patient, the color of the first body and the color of the second body being the same if the source and patient blood types match.

9. An assembly according to claim 4, in which said additional means comprises additional cylindrical projections on said first body extending from its flat face at given radial distances from the axis of said body and of given diameters, and additional bores on said second body at given radial distances from its axis and of given internal diameters, the circumferential spacing between the projections and bores on the first and second bodies respectively being the same and the diameters matching only if the source and patient blood types match.

10. An assembly according to claim 4, in which said additional means includes radial ears at a given circumferential spacing from each other on said first body, and radial slots on said second body at a given circumferential distance from each other, the circumferential spacing of said slots being equal to the circumferential distance of said ears so that the ears can be received in the slot only if the source and the patient blood types match.

11. An assembly according to claim 1 in which said additonal means includes at least one annular exterior channel on each of said first connectors and at least one annular exterior channel on each of said second connectors, the number of said channels on said first and second connectors being equal only when the source and patient blood type match.

12. An assembly according to claim 1 in which said additonal means includes at least one annular rib on each of said first connectors and at least one annular rib on each of said second connectors, the number of annular ribs on said first and second connectors being equal only when the source and patient blood type match.

13. An assembly according to claim 1 in which said additional means comprises nomenclature on each of said first connectors indicating the blood type of the source and nomenclature on each of said second connectors indicating the blood type of the patient.

14. An assembly according to claim 1 in which said additional means comprises an exterior color on each of said first connectors characteristic of the blood type of the source and an exterior color on each of said second connectors characteristic of the blood type of the patient, the color of the first connector and the color of the second connector being the same when the source and patient blood types match.

15. An assembly according to claim 1 in which said additonal means includes radial ears at a given circumferential spacing from each other on each of said first connectors and radial slots at a given circumferential distance from each other on each of said second connectors, the circumferential spacing of said slots being equal to the circumferential distance of said ears so that the ears can be received in the slots only if the source and the patient blood types match.

16. A connector assembly system for use in assuring a proper blood type match when transfusing blood from a source to a patient, comprising:
   (a) a plurality of first male connectors adapted to communicate with a respective plurality of blood sources of different blood type, said first connectors each including a blood carrying projection of first given dimensions different from the first given dimensions of the remaining ones of said first connectors;
   (b) a plurality of second female connectors corresponding in number with the plurality of first connectors and adapted respectively to communicate with the blood streams of a plurality of patients having different blood types, said second connectors each including a blood carrying bore of second given dimensions different from the second given dimensions of the remaining ones of said second connectors, said second given dimensions for each of said second connectors being complementary with said first given dimensions of only a respective one of said first connectors so that a mating blood carrying connection between one of said first connectors and one of said second connectors can be made only if the source and patient blood types match; and additional means on each of said first connectors and on each of said second connectors for indicating the source and patient blood type respectively associated therewith.

* * * * *